US012778972B2

(12) United States Patent
Blanchard et al.

(10) Patent No.: US 12,778,972 B2
(45) Date of Patent: Nov. 3, 2026

(54) NUTRITIONAL COMPOSITION COMPRISING HUMAN MILK OLIGOSACCHARIDES

(71) Applicant: SOCIETE DES PRODUITS NESTLE S.A., Vevey (CH)

(72) Inventors: Carine Blanchard, Le Mont-sur-Lausanne (CH); Sebastien Holvoet, Montpreveyres (CH); Dominique Sandra Donnicola, Servion (CH); Cheong Kwet Choy Kwong Chung, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 779 days.

(21) Appl. No.: 18/248,942

(22) PCT Filed: Oct. 7, 2021

(86) PCT No.: PCT/EP2021/077653
§ 371 (c)(1),
(2) Date: Apr. 13, 2023

(87) PCT Pub. No.: WO2022/078859
PCT Pub. Date: Apr. 21, 2022

(65) Prior Publication Data

US 2023/0381211 A1 Nov. 30, 2023

(30) Foreign Application Priority Data

Oct. 16, 2020 (EP) .................................... 20202262

(51) Int. Cl.

| | |
|---|---|
| ***A61K 31/702*** | (2006.01) |
| ***A23L 33/00*** | (2016.01) |
| ***A23L 33/125*** | (2016.01) |
| ***A61K 9/00*** | (2006.01) |
| ***A61P 37/08*** | (2006.01) |

(52) U.S. Cl.
CPC .......... *A61K 31/702* (2013.01); *A23L 33/125* (2016.08); *A23L 33/40* (2016.08); *A61K 9/0056* (2013.01); *A61P 37/08* (2018.01)

(58) Field of Classification Search
None
See application file for complete search history.

(56) References Cited

U.S. PATENT DOCUMENTS

| | | | | |
|---|---|---|---|---|
| 11,602,545 B2 * | 3/2023 | McConnell | ............... | A61P 1/00 |
| 2012/0172307 A1 | 7/2012 | Davis et al. | | |
| 2015/0183814 A1 * | 7/2015 | Schroven | ............... | A23L 33/10 536/53 |
| 2018/0333426 A1 * | 11/2018 | Chichlowski | ........... | A23L 33/40 |
| 2020/0384041 A1 * | 12/2020 | Jennewein | ............ | A23L 33/125 |

FOREIGN PATENT DOCUMENTS

| | | |
|---|---|---|
| CN | 103384525 A | 11/2013 |
| CN | 104363962 A | 2/2015 |
| CN | 104853621 A | 8/2015 |
| CN | 104955344 A | 9/2015 |
| CN | 105682664 A | 6/2016 |
| CN | 105722514 A | 6/2016 |
| CN | 108471793 A | 8/2018 |
| EP | 2454948 | 5/2012 |
| IN | 201917014627 A | 7/2019 |
| WO | 2014100022 A1 | 6/2014 |
| WO | 2015077233 | 5/2015 |
| WO | 2017103019 | 6/2017 |
| WO | 2019038668 | 2/2019 |

OTHER PUBLICATIONS

Akdis, C. A., & Akdis, M. (2014). Mechanisms of immune tolerance to allergens: role of IL-10 and Tregs. The Journal of clinical investigation, 124(11), 4678-4680. (Year: 2014).*
Chinese Office Action for Appl No. 202180067936.4 dated Jan. 9, 2025, 9 pages.
Austin et al. "Temporal Change of the Content of 10 Oligosaccharides in the Milk of Chinese Urban Mothers" Nutrients, Jun. 8, 2016, vol. 8, No. 6, 22 pages.
Wicinski et al. "Human Milk Oligosaccharides: Health Benefits, Potential Applications in Infant Formulas, and Pharmacology" Nutrients, Jan. 20, 2020, vol. 12, No. 1, 14 pages.
Xiao Ling et al., "Human milk oligosaccharides promote immune tolerance via direct interactions with human dendritic cells" Eur. Immunol. 2019. 49: 1001-1014.

* cited by examiner

*Primary Examiner* — Dale R Miller
(74) *Attorney, Agent, or Firm* — K&L Gates LLP

(57) ABSTRACT

A nutritional composition comprising the human milk oligosaccharides (HMOs) 2'-fucosyllactose (2FL), 3'-fucosyllactose (3FL), 3-sialyllactose (SSL), and lacto-N-neotetraose (LNnT). The nutritional composition is useful for inducing tolerance to an allergen, and/or speeding up outgrowth of an allergy, and/or treating or reducing the risk of an interleukin IL-10 mediated disease.

20 Claims, 3 Drawing Sheets

NUTRITIONAL COMPOSITION COMPRISING HUMAN MILK OLIGOSACCHARIDES

CROSS REFERENCE TO RELATED APPLICATIONS

The present application is a National Stage of International Application No. PCT/EP2021/077653, filed on Oct. 7, 2021, which claims priority to European Patent Application No. 20202262.0, filed on Oct. 16, 2020, the entire contents of which are being incorporated herein by reference.

FIELD OF THE INVENTION

The present invention relates to nutritional compositions for use in inducing tolerance to an allergen. In particular, the invention relates to nutritional compositions comprising the human milk oligosaccharides (HMOs) 2'-fucosyllactose (2FL), 3'-fucosyllactose (3FL), 3'-sialyllactose (3SL), lacto-N-neotetraose (LNnT), and optionally 6'-sialyllactose (6SL) and lacto-N-tetraose (LNT).

BACKGROUND TO THE INVENTION

The incidence of allergic diseases such as food allergy, atopic dermatitis and asthma is increasing globally. For example, 300 million people worldwide suffer from asthma, and in the European Union 11-26 million people have a food allergy (Martins, T. B. et al. (2014) J Allergy Clin Immunol 133: 589-91).

Cow's milk protein (CMP) is the leading cause of food allergy in infants, affecting 2-3% children worldwide. Most children with CMP-allergy (CMPA) have two or more symptoms: 50-70% have skin symptoms; 50-60% have gastrointestinal symptoms; and 20-30% have airway symptoms. Severe and life-threatening symptoms may occur in 10% of children. (Nutten, 2018. EMJ Allergy Immunol, 3(1), pp. 50-59).

There is growing evidence regarding the role of infant gut microbial composition in the immune trajectory and allergy development of the infant host (Quante M. et al. (2012) BMC Public Health 12: 1021). As such, environmental factors such as diet, pollution, urban lifestyle, cleanliness and birth method have been associated with the development of the immune system and allergic diseases (Seppo, A. E. et al. (2017) J Allergy Clin Immunol 139: 708-11 e5; Azad, M. B. et al. (2018) J Nutr 148: 1733-42).

Breast milk is an immunologically active fluid, which contains a host of components that may modulate the development of the immune system and, in turn, the development of allergic disease. The influence of human milk oligosaccharides (HMOs), the third most abundant component in breast milk, in the development of allergic disease has been of particular interest. HMOs are structurally varied lactose-based complex glycans that include both short- and long-chain oligosaccharides. The number (over 200 HMOs have been identified) and structural diversity of HMOs in human breast milk are not observed in other mammalian milks.

HMO composition is influenced by both environmental and genetic influences and varies greatly across maternal populations. Synthesised in the mammary glands, HMO quantity in breast milk ranges from about 20.9 g/L in colostrum to 12.9 g/L in mature milk. Association studies have led to the identification of some breast milk levels of HMOs that correlate with milk or food allergy in infants. However, there has remained uncertainty over the identity of particular HMOs that may be beneficial in modulating allergy.

Human breast milk and breast feeding are considered to be the optimal form of nutrition for healthy infants during the first months of life. However, there is a need for nutritional sources that can be used in addition to breast milk. Furthermore, not all infants can be breast fed and the needs of more vulnerable infants, such as preterm infants, cannot be achieved by their mother's milk, so there is also a need for alternatives to breast milk. Nutritional compositions, such as infant formulas, that satisfy the nutritional requirements of infants may be used as a substitute for or complement to human breast milk. However, the composition of infant formulas must be carefully controlled to satisfy nutritional requirements, provide acceptable taste and further aid the development of infants, particularly when targeted to infants who are allergic or at risk of allergy.

There remains a significant need for nutritional compositions that are suitable for allergic infants and children. In particular, there is a need for formulas that are effective in inducing tolerance to allergens and speeding up outgrowth of an allergy, particularly cow's milk allergy.

SUMMARY OF THE INVENTION

The present inventors have surprisingly found that specific combinations of HMOs are most efficacious in inducing IL-10. The combinations have utility in reducing allergic sensitisation and inducing tolerance to allergens.

Accordingly, in one aspect, the invention provides a nutritional composition comprising the human milk oligosaccharides (HMOs) 2'-fucosyllactose (2FL), 3'-fucosyllactose (3FL), 3'-sialyllactose (3SL), and lacto-N-neotetraose (LNnT).

In some embodiments, the the HMOs in the nutritional composition consist of, or consist essentially of, 2FL, 3FL, 3SL, and LNnT.

In some embodiments, the HMOs in the nutritional composition consist of, or consist essentially of:

i. about 40 wt % to about 80 wt % of 2FL, preferably about 55 wt % to about 75 wt %, preferably about 65 wt % to about 70 wt %;
ii. about 2 wt % to about 15 wt % of LNnT, preferably about 4 wt % to about 12 wt %, preferably about 6 wt % to about 9 wt %;
iii. about 5 wt % to about 30 wt % 3FL, preferably about 10 wt % to about 25 wt %, preferably about 15 wt % to about 20 wt %; and
iv. about 2 wt % to about 15 wt % of 3SL; preferably about 4 wt % to about 12 wt %, preferably about 7 wt % to about 9 wt %.

In some embodiments, the total amount of 2FL, 3FL, 3SL, and LNnT present in the nutritional composition is at a concentration of between 10 µg/ml and 10000 µg/ml, preferably between 50 µg/ml and 5000 µg/ml.

In another aspect, the invention provides a nutritional composition comprising the human milk oligosaccharides (HMOs) 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT).

In some embodiments, the HMOs in the nutritional composition consist of, or consist essentially of, 2FL, 3FL, 3SL, LNnT, 6SL and LNT.

In some embodiments, the HMOs in the nutritional composition consist of, or consist essential of:

i. about 35 wt % to about 60 wt % of 2FL, preferably about 40 wt % to about 50 wt %, preferably about 43 wt % to about 47 wt %;
ii. about 1 wt % to about 10 wt % of LNnT, preferably about 3 wt % to about 7 wt %, preferably about 4 wt % to about 6 wt %;
iii. about 10 wt % to about 30 wt % of LNT, preferably about 15 wt % to about 25 wt %, preferably about 18 wt % to about 22 wt %;
iv. about 3 wt % to about 20 wt % 3FL, preferably about 7 wt % to about 15 wt %, preferably about 10 wt % to about 13 wt %;
v. about 1 wt % to about 10 wt % of 3SL, preferably about 4 wt % to about 8 wt %, preferably about 5 wt % to about 7 wt %; and
vi. about 5 wt % to about 20 wt % of 6SL, preferably about 7 wt % to about 15 wt %, preferably about 10 wt % to about 14 wt %.

In some embodiments, the total amount of 2FL, 3FL, 3SL, LNnT, 6SL and LNT present in the nutritional composition is at a concentration of between 10 μg/ml and 10000 μg/ml, preferably between 50 μg/ml and 5000 μg/ml.

The nutritional composition of the invention is preferably for administration to an infant or a young-child.

In an embodiment the nutritional composition may be in the form of an infant formula, a starter infant formula, a follow-on or follow-up infant formula, a growing-up milk, a fortifier or a supplement. In one embodiment, the nutritional composition of the invention is an infant formula or a young-child formula.

In some embodiments, the nutritional composition of the invention is an extensively hydrolysed formula (eHF) or an amino acid-based formula (AAF).

In some embodiments, the nutritional composition of the invention comprises:

(a) 1.8-3.2 g protein per 100 kcal;
(b) 9-14 g carbohydrate per 100 kcal; and/or
(c) 4.0-6.0 g fat per 100 kcal.

In some embodiments, the nutritional composition of the invention comprises about 2.4 g or less protein per 100 kcal.

In some embodiments, the nutritional composition of the invention comprises 1.8-2.4 g protein per 100 kcal, 2.1-2.3 g protein per 100 kcal, or 2.15-2.25 g protein per 100 kcal.

In some embodiments, the nutritional composition comprises about 2.2 g protein per 100 kcal.

In some embodiments, about 30% or less by weight of the fat in the nutritional composition of the invention is medium chain triglycerides (MCTs).

In some embodiments the nutritional composition is a supplement. In one embodiment, the 30 total amount of 2FL, 3FL, 3SL, and LNnT present in the supplement may be in an amount of 0.2 g to 2 g per unit dose of the supplement, preferably about 0.4 g to 1.5 g per unit dose, preferably between 0.5 g and 1 g per unit dose. In one embodiment, the total amount of 2FL, 3FL, 3SL, LNnT, 6SL and LNT present in the supplement may be in an amount of 0.2 g to 2 g per unit dose of the supplement, preferably about 0.4 g to 1.5 g per unit dose, preferably between 0.5 g and 1 g per unit dose.

In another aspect, there is provided a nutritional composition as defined herein for use in inducing tolerance to an allergen, preferably a food allergen. In one embodiment the allergen is cow's milk protein.

In one aspect, the invention provides a method of inducing a subject's tolerance to an allergen, preferably a food allergen. In an embodiment the allergen is cow's milk protein, comprising administering to the subject a nutritional composition as defined herein. Preferably the subject is an infant or child.

In another aspect, there is provided a nutritional composition as defined herein for use in speeding up outgrowth of an allergy, preferably an allergy to a food allergen. In one embodiment the allergy is cow's milk allergy.

In one aspect the invention provides a method of speeding up outgrowth of an allergy in a subject comprising administering to the subject a nutritional composition as defined herein. Preferably the subject is an infant or child.

In another aspect, there is provided a nutritional composition as defined herein for use in treating an interleukin IL-10 mediated disease.

In one aspect the invention provides a method of treating, preventing or reducing the risk of an interleukin IL-10 mediated disease in a subject comprising administering a nutritional composition as defined herein to the subject. Preferably the subject is an infant or child.

In one aspect the invention provides a method of increasing the expression of interleukin IL-10 in a subject comprising administering a nutritional composition as defined herein to the subject. Preferably the subject is an infant or child.

DETAILED DESCRIPTION OF THE INVENTION

Figure 1:
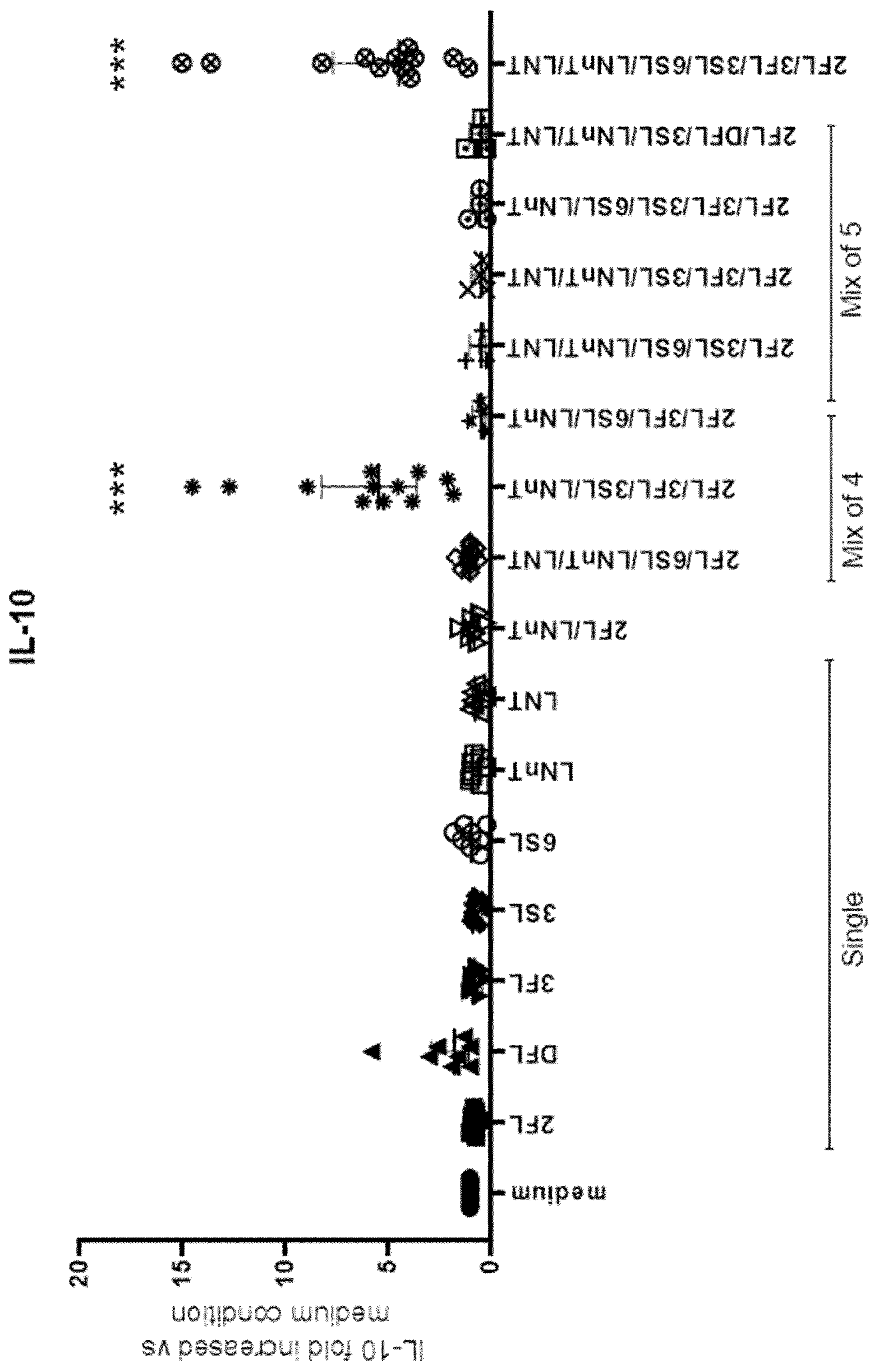
FIG. 1—HMOs induced IL-10 expression level in peripheral blood mononuclear cells. PBMCs were skewed toward a TH2 phenotype and different HMO mixes tested. The level of IL-10 was quantified in the supernatants following HMO mixes incubation.

Various preferred features and embodiments of the present invention will now be described by way of non-limiting examples.

It must be noted that as used herein and in the appended claims, the singular forms "a", "an", and "the" include plural referents unless the context clearly dictates otherwise.

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the terms "consisting of" and "consisting essentially of".

The term "consisting essentially of" as used herein means that any additional, non-recited members, elements or steps do not materially affect the characteristics of the claimed apparatus, composition, method, etc. Suitably, a composition comprising HMOs which "consist essentially of" recited HMOs may comprise trace amounts of non-recited HMOs (e.g. less than 1% by weight, less by 0.5% by weight, or less than 0.1% by weight of total HMOs) which do not materially affect the characteristics of the composition.

As used herein the term "about" means approximately, in the region of, roughly, or around. When the term "about" is used in conjunction with a numerical value or range, it modifies that value or range by extending the boundaries above and below the numerical value(s) set forth. In general, the terms "about" and "approximately" are used herein to modify a numerical value(s) above and below the stated value(s) by 10%.

The publications discussed herein are provided solely for their disclosure prior to the filing date of the present application. Nothing herein is to be construed as an admission that such publications constitute prior art to the claims appended hereto.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

Nutritional Composition

The expression "nutritional composition" means a composition which nourishes a subject.

This nutritional composition is usually to be taken orally and it usually includes a lipid or fat source and a protein source.

In a particular embodiment, the nutritional composition is a synthetic nutritional composition. The expression "synthetic nutritional composition" means a mixture obtained by chemical and/or biological means, which can be chemically identical to the mixture naturally occurring in mammalian milks (i.e. the synthetic nutritional composition is not breast milk).

In a preferred embodiment, the nutritional composition is for an infant or young child. The infant may be, for example, 0-1 years of age or 0-6 months of age. The child may be, for example, 1-3 years of age. In a particularly preferred embodiment, the nutritional composition is an infant formula or a young-child formula.

The term "infant formula" may refer to a foodstuff intended for particular nutritional use by infants during the first year of life and satisfying by itself the nutritional requirements of this category of person, as defined in European Commission Regulation (EU) 2016/127 of 25 Sep. 2015.

The expression "infant formula" encompasses both "starter infant formula" and "follow-up formula" or "follow-on formula".

A "follow-up formula" or "follow-on formula" is given from the $6^{th}$ month onwards.

The infant formula of the present invention may be a hypoallergenic infant formula. The infant formula of the present invention may be an extensively hydrolysed infant formula (eHF) or an amino acid-based infant formula (AAF). Alternatively, the infant formula may be a partially hydrolysed infant formula (pHF).

The term "extensively hydrolysed formula" or "eHF" may refer to a formula comprising extensively hydrolysed protein. The eHF may be a hypoallergenic infant formula which provides complete nutrition for infants who cannot digest intact cow's milk protein (CMP) or who are intolerant or allergic to CMP.

The term "amino acid-based formula" or "AAF" may refer to a formula comprising only free amino acids as a protein source. The AAF may contain no detectable peptides. The AAF may be a hypoallergenic infant formula which provides complete nutrition for infants with food protein allergy and/or food protein intolerance. For example, the AAF may be a hypoallergenic infant formula which provides complete nutrition for infants who cannot digest intact CMP or who are intolerant or allergic to CMP, and who may have extremely severe or life-threatening symptoms and/or sensitisation against multiple foods.

A "hypoallergenic" composition is a composition which is unlikely to cause allergic reactions. A hypoallergenic infant formula may be tolerated by more than 90% of infants with CMP allergy. This is in line with the guidance provided by the American Academy of Pediatrics (Committee on Nutrition, 2000. Pediatrics, 106(2), pp. 346-349). Such an infant formula may not contain peptides which are recognized by CMP-specific IgE e.g. IgE from subjects with CMPA.

Infants can be fed solely with the infant formula or the infant formula can be used as a complement of human milk.

The term "young-child formula" may refer to a foodstuff intended to partially satisfy the nutritional requirements of young children ages 1 to 3 years. The expression "young-child formula" encompasses "toddler's milk", "growing up milk", or "formula for young children". The ESPGHAN Committee on Nutrition has recently reviewed young-child formula (Hojsak, I., et al., 2018. Journal of pediatric gastroenterology and nutrition, 66(1), pp. 177-185). Suitably, a young-child formula may meet the compositional requirements proposed in Hojsak, I., et al., 2018. Journal of pediatric gastroenterology and nutrition, 66(1), pp. 177-185 and/or Suthutvoravut, U., et al., 2015. Annals of Nutrition and Metabolism, 67(2), pp. 119-132.

The young-child formula of the present invention may be a hypoallergenic young-child formula. The young-child formula of the present invention may be an extensively hydrolysed young-child formula or an amino acid-based young-child formula. Alternatively, the young-child formula may be a partially hydrolysed young-child formula (pHF).

The infant formula or a young-child formula of the invention may be in the form of a powder or liquid.

The liquid may be, for example, a concentrated liquid formula or a ready-to-feed formula. The formula may be in the form of a reconstituted infant or young-child formula (i.e. a liquid formula that has been reconstituted from a powdered form). The concentrated liquid infant or young-child formula is preferably capable of being diluted into a liquid composition suitable for feeding an infant or child, for example by the addition of water.

In some embodiments, the infant or young-child formula is in a powdered form. The powder is capable of being reconstituted into a liquid composition suitable for feeding an infant or child, for example by the addition of water.

The nutritional composition may have an energy density of about 60-72 kcal per 100 mL, when formulated as instructed. Suitably, the nutritional composition may have an energy density of about 60-70 kcal per 100 mL, when formulated as instructed.

The nutritional composition according to the invention can be for example an infant formula, a starter infant formula, a follow-on or follow-up formula, a fortifier such as a human milk fortifier, or a supplement. In some particular embodiments, the composition of the invention is an infant formula, a young-child formula or a supplement. In one preferred embodiment the nutritional composition of the invention is an infant formula.

Within the context of the present invention, the term "fortifier" refers to a composition which comprises one or more nutrients having a nutritional benefit for infants. By the term "milk fortifier", it is meant any composition used to fortify or supplement either human breast milk, infant formula, growing-up milk or human breast milk fortified with other nutrients. Accordingly, the human milk fortifier of the present invention can be administered after dissolution in human breast milk, infant formula, growing-up milk or human breast milk fortified with other nutrients or otherwise it can be administered as a stand alone composition.

When administered as a stand-alone composition, the human milk fortifier of the present invention can be also identified as being a "supplement". In one embodiment, the milk fortifier of the present invention is a supplement. In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition of the present invention can be in solid (e.g. powder), liquid or gelatinous form.

Human Milk Oligosaccharides

The nutritional composition of the invention contains human milk oligosaccharides (HMOs).

Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk. Almost all HMOs have a lactose moiety at their reducing end while sialic acid and/or fucose (when present) occupy terminal positions at the non-reducing ends. HMOs can be acidic (e.g. charged sialic acid containing oligosaccharides) or neutral (e.g. fucosylated oligosaccharides).

In some embodiments, HMOs in the nutritional composition comprise, consist essentially of, or preferably consist of 2'-fucosyllactose (2FL), 3'-fucosyllactose (3FL), 3'-sialyllactose (3SL) and lacto-N-neotetraose (LNnT). Thus, the nutritional composition may comprise no other type of HMO aside from 2FL, 3FL, 3SL and LNnT.

In another embodiment, the HMOs in the nutritional composition comprise, consist essentially of, or preferably consist of 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT). Thus, the nutritional composition may comprise no other type of HMO aside from 2FL, 3FL, 3SL, LNnT, 6SL and LNT.

The HMOs may be obtained by any suitable method. Suitable methods for synthesising HMOs will be well known to those of skill in the art. For example, processes have been developed for producing HMOs by microbial fermentations, enzymatic processes, chemical syntheses, or combinations of these technologies (Zeuner et al., 2019. Molecules, 24(11), p. 2033).

The 2FL may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Alternatively, 2FL may be produced by chemical synthesis from lactose and free fucose.

The 3FL may be synthesized by enzymatic, biotechnological and/or chemical processes. The 3FL may be manufactured through fermentation using a genetically modified microorganism. Alternatively, the 3FL may be produced as described in WO 2013/139344.

The 3SL may be synthesized by enzymatic, biotechnological and/or chemical processes. The 3SL may be produced as described in WO 2014/153253.

The LNnT may be synthesised chemically by enzymatic transfer of saccharide units from donor moieties to acceptor moieties using glycosyltransferases as described, for example, in U.S. Pat. No. 5,288,637 and WO 1996/010086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M. and Stutz, A. E. (1999) Angew. Chem. Int. Ed. 38: 827-828. N-acetyl-lactosamine produced in this way may then be transferred to lactose as the acceptor moiety. Alternatively, the LNnT may be produced as described in WO 2011/100980 or WO 2013/044928.

The 6SL may be synthesized by chemical methods including stereoselective 6'-O-sialylation of either 4',6'-sugar diols or 6'-sugar alcohols using glycosylhalide, thioglycoside or diethylphosphite donor activations. Alternatively, the 6SL may be enzymatically produced using glycosyltransferases and sialidases. The 6SL may be produced as described in WO 2011/100979.

The LNT may be synthesized by enzymatic, biotechnological and/or chemical processes. The LNT may be produced as described in WO 2012/155916 or WO 2013/044928. A mixture of LNT and LNnT can be made as described in WO 2013/091660.

In some embodiments the nutritional composition comprises the human milk oligosaccharides (HMOs) 2'-fucosyllactose (2FL), 3'-fucosyllactose (3FL), 3'-sialyllactose (3SL), and lacto-N-neotetraose (LNnT). In some embodiments, the HMOs in the nutritional composition consist of, or consist essentially of, 2FL, 3FL, 3SL, and LNnT.

In some embodiments, the HMOs in the nutritional composition consist of, or consist essentially of:

i. about 40 wt % to about 80 wt % of 2FL, preferably about 55 wt % to about 75 wt %, preferably about 65 wt % to about 70 wt %;
ii. about 2 wt % to about 15 wt % of LNnT, preferably about 4 wt % to about 12 wt %, preferably about 6 wt % to about 9 wt %;
iii. about 5 wt % to about 30 wt % 3FL, preferably about 10 wt % to about 25 wt %, preferably about 15 wt % to about 20 wt %; and
iv. about 2 wt % to about 15 wt % of 3SL; preferably about 4 wt % to about 12 wt %, preferably about 7 wt % to about 9 wt %.

In some embodiments, the total amount of 2FL, 3FL, 3SL, and LNnT present in the nutritional composition is at a concentration of between 1 μg/ml and 5000 μg/ml, preferably between 10 μg/ml and 100 μg/ml. In some embodiments, the total amount of 2FL, 3FL, 3SL, and LNnT present in the nutritional composition is at a concentration of between 1 μg/kcal and 10000 μg/kcal, preferably between 10 μg/kcal and 200 μg/kcal.

In some embodiments the invention provides a nutritional composition comprising the human milk oligosaccharides (HMOs) 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT). In some embodiments, the HMOs in the nutritional composition consist of, or consist essentially of, 2FL, 3FL, 3SL, LNnT, 6SL and LNT.

In some embodiments, the HMOs in the nutritional composition consist of, or consist essential of:

i. about 35 wt % to about 60 wt % of 2FL, preferably about 40 wt % to about 50 wt %, preferably about 43 wt % to about 47 wt %;
ii. about 1 wt % to about 10 wt % of LNnT, preferably about 3 wt % to about 7 wt %, preferably about 4 wt % to about 6 wt %;
iii. about 10 wt % to about 30 wt % of LNT, preferably about 15 wt % to about 25 wt %, preferably about 18 wt % to about 22 wt %;
iv. about 3 wt % to about 20 wt % 3FL, preferably about 7 wt % to about 15 wt %, preferably about 10 wt % to about 13 wt %;
v. about 1 wt % to about 10 wt % of 3SL, preferably about 4 wt % to about 8 wt %, preferably about 5 wt % to about 7 wt %; and
vi. about 5 wt % to about 20 wt % of 6SL, preferably about 7 wt % to about 15 wt %, preferably about 10 wt % to about 14 wt %.

In some embodiments, in particular where the nutritional composition is an infant formula or a young-child formula, the total amount of 2FL, 3FL, 3SL, and LNnT present in the nutritional composition is at a concentration of between 10 μg/ml and 10000 μg/ml, preferably between 50 μg/ml and 5000 μg/ml (when formulated as instructed).

In some embodiments, in particular where the nutritional composition is an infant formula or a young-child formula, the total amount of 2FL, 3FL, 3SL, LNnT, 6SL and LNT present in the nutritional composition is at a concentration of between 10 μg/ml and 10000 μg/ml, preferably between 50 μg/ml and 5000 μg/ml (when formulated as instructed).

In some embodiments, when the nutritional composition is in the form of a supplement, the total amount of 2FL, 3FL, 3SL, and LNnT, or of 2FL, 3FL, 3SL, LNnT, 6SL and LNT, present in the supplement may be in an amount of 0.2 g to 2 g per unit dose of the supplement, preferably about 0.4 g to 1.5 g per unit dose, preferably between 0.5 g and 1 g per unit dose. In one embodiment, when the nutritional composition is in the form of a supplement, the total amount of 2FL, 3FL, 3SL, and LNnT, or total amount of 2FL, 3FL, 3SL, LNnT, 6SL and LNT, present in the supplement may be in an amount of 0.7 g to 0.8 g per unit dose of the supplement.

In a particular embodiment of the present invention, the nutritional composition comprises the 2'-fucosyllactose (2FL) and lacto-N-neotetraose (LNnT) in a 2FL:LNnT weight ratio from 1:10 to 12:1, such as from 1:7 to 10:1 or from 1:5 to 5:1 or from 2:1 to 5:1 or from 1:3 to 3:1, or from 1:2 to 2:1, or from 1:1 to 3:1, or from 1:5 to 1:0.5; for example 2:1 or 10:1. In a particular embodiment of the present invention, the nutritional composition comprises the 2'-fucosyllactose (2FL) and lacto-N-neotetraose (LNnT) in a 2FL:LNnT weight ratio of about 2:1.

Protein

The term "protein" includes peptides and free amino acids. The protein content of the nutritional composition may be calculated by any method known to those of skill in the art. Suitably, the protein content may be determined by a nitrogen-to-protein conversion method. For example, as described in Maubois, J. L. and Lorient, D. (2016) Dairy Science & Technology 96(1): 15-25. Preferably the protein content is calculated as nitrogen content×6.25, as defined in European Commission Regulation (EU) 2016/127 of 25 Sep. 2015. The nitrogen content may be determined by any method known to those of skill in the art. For example, nitrogen content may be measured by the Kjeldahl method.

The protein content of the nutritional composition of the invention, particularly the infant formula of the invention, is preferably in the range 1.6-3.2 g protein per 100 kcal. In some embodiments, the protein content of the nutritional composition is in the range 1.8-2.8 g protein per 100 kcal.

eHFs typically contain 2.6-2.8 g protein per 100 kcal and AAFs typically contain 2.8-3.1 g protein per 100 kcal, for example to cover the needs of infants suffering gastrointestinal pathologies with severe malabsorption or infants requiring more proteins and calories to cover a higher metabolic rate.

Infant formulas, such as an eHF or an AAF, with a lower protein content may support appropriate growth and development of allergic infants, as well as being safe and well-tolerated.

Accordingly, in some embodiments, the nutritional composition of the invention, particularly the infant formula of the invention, may comprise about 2.4 g or less protein per 100 kcal. For example, the nutritional composition may comprise about 2.3 g or less protein per 100 kcal, 2.25 g or less protein per 100 kcal, or 2.2 g or less protein per 100 kcal.

Suitably, the nutritional composition of the invention, particularly the infant formula of the invention, comprises about 1.8 g or more protein per 100 kcal. For example, the nutritional composition may comprise about 1.86 g or more protein per 100 kcal, 1.9 g or more protein per 100 kcal, 2.0 g or more protein per 100 kcal, or 2.1 g or more protein per 100 kcal. In some embodiments, the nutritional composition comprises about 1.86 g or more protein per 100 kcal, in line with present EU regulations for infant formula (EFSA NDA Panel (2014) EFSA journal 12(7): 3760).

In some embodiments, the nutritional composition of the invention, particularly the infant formula of the invention, may comprise 1.8-2.4 g protein per 100 kcal, 1.86-2.4 g protein per 100 kcal, 1.9-2.4 g protein per 100 kcal, 2.0-2.4 g protein per 100 kcal, 2.0-2.3 g protein per 100 kcal, 2.1-2.3 g protein per 100 kcal, or 2.15-2.25 g protein per 100 kcal.

Protein Source

The source of protein may be any source suitable for use in a nutritional composition.

In some embodiments, the protein is cow's milk protein. In some embodiments, the nutritional composition does not comprise cow's milk protein In some embodiments, the nutritional composition does not comprise dairy protein. Accordingly, in some embodiments, 100% by weight of the total protein is non-dairy protein.

An extensively hydrolysed/hydrolysed whey-based formula may be more palatable than an extensively hydrolysed/hydrolysed casein-based formula and/or the subject may only be sensitised to casein protein. Suitably, therefore, more than about 50%, more than about 60%, more than about 70%, more than about 80%, more than about 90%, or about 100% of the protein is whey protein. Preferably, the protein source is whey protein.

The whey protein may be a whey from cheese making, particularly a sweet whey such as that resulting from the coagulation of casein by rennet, an acidic whey from the coagulation of casein by an acid, or the acidifying ferments, or even a mixed whey resulting from coagulation by an acid and by rennet. This starting material may be whey that has been demineralised by ion exchange and/or by electrodialysis and is known as demineralised whey protein (DWP).

The source of the whey protein may be sweet whey from which the caseino-glycomacropeptide (CGMP) has been totally or partially removed. This is called modified sweet whey (MSW). Removal of the CGMP from sweet whey results in a protein material with threonine and trytophan contents that are closer to those of human milk. A process for removing CGMP from sweet whey is described in EP880902.

The whey protein may be a mix of DWP and MSW.

In some embodiments, the amount of casein in the nutritional composition is undetectable, for example less than 0.2 mg/kg. The amount of casein may be determined by any method known to those of skill in the art.

Degree of Hydrolysis

Hydrolysed proteins may be characterised as "partially hydrolysed" or "extensively hydrolysed" depending on the degree to which the hydrolysis reaction is carried out. Currently there is no agreed legal/clinical definition of Extensively Hydrolyzed Products according to the WAO (World Allergy Organization) guidelines for Cow's milk protein allergy (CMA) but there is agreement that according to the WAO that hydrolysed formulas have proven to be a useful and widely used protein source for infants suffering from CMA. In the current invention partially hydrolysed proteins are one in which 60-70% of the protein/peptide population has a molecular weight of less than 1000 Daltons, whereas extensively hydrolysed proteins are one in which at least 95% of the protein/peptide population has a molecular weight of less than 1000 Dalton. These definitions are currently used in the industry. Partially hydrolysed proteins are usually considered as hypoallergenic (HA) whereas extensively hydrolysed proteins are usually considered as non-allergenic.

The hydrolysed proteins of the invention may have an extent of hydrolysis that is characterised by NPN/TN %. Non-Protein Nitrogen over Total Nitrogen is widely use as a measure of soluble peptides created by enzymatic hydrolysis. NPN/TN % means the Non Protein Nitrogen divided by the Total Nitrogen X 100. NPN/TN % may be measured as detailed in Adler-Nissen J-, 1979, J. Agric. Food Chem., 27 (6), 1256-1262. In general, extensively hydrolysed proteins are characterised as having a NPN/TN % of greater than 95%, whereas partially hydrolysed proteins are characterized as having a NPN/TN % in the range 75%-85%. Partially hydrolysed proteins may also be characterised in that 60-70% of their protein/peptide population has a molecular weight of less than 1000 Daltons.

In a preferred embodiment, the protein may have an NPN/TN % greater than 90%, greater than 95% or greater than 98%. In a preferred embodiment where "extensively" hydrolysed proteins are desired the hydrolysed proteins of the invention has a NPN/TN % in the range of greater than 95%. Suitably, the protein may have an NPN/TN % greater than 90%, greater than 95% or greater than 98%. These extensively hydrolysed proteins may also be characterised in that at least 95% of their protein/peptide population has a molecular weight of less than 1000 Daltons.

The extent of hydrolysis may also be determined by the degree of hydrolysis. The "degree of hydrolysis" (DH) is defined as the proportion of cleaved peptide bonds in a protein hydrolysate and may be determined by any method known to those of skill in the art. Suitably the degree of hydrolysis is determined by pH-stat, trinitrobenzenesulfonic acid (TNBS), o-phthaldialdehyde (OPA), trichloroacetic acid soluble nitrogen (SN-TCA), or formol titration methods. (Rutherfurd, S. M. (2010) Journal of AOAC International 93(5): 1515-1522). The degree of hydrolysis (DH) of the protein can, for example, be more than 90, more than 95 or more than 98.

The extent of hydrolysis may also be determined by the peptide molecular mass distribution. The peptide molecular mass distribution may be determined by high performance size exclusion chromatography, optionally with UV detection (HPSEC/UV) (Johns, P. W. et al. (2011) Food chemistry 125(3): 1041-1050). For example, the peptide molecular mass distribution may be a HPSEC peak area-based estimate determined at 205 nm, 214 nm or 220 nm. Suitably when the peptide molecular mass distribution is determined by HPSEC/UV, the "percentage of peptides by weight" that have a certain molecular mass may be estimated by the "fraction of peak area as a percentage of total peak area", that have the molecular mass, determined at 205 nm, 214 nm or 220 nm. Suitably, the extent of hydrolysis may be determined by the methods described in WO 2016/156077. Alternatively, the peptide molecular mass distribution may be determined by any method known to those of skill in the art, for example by sodium dodecyl sulphate-polyacrylamide gel electrophoresis (SDS-PAGE) (Chauveau, A. et al. (2016) Pediatric Allergy and Immunology 27(5): 541-543).

Theoretically, to bind with cell membrane-bound IgE, peptides should be greater than about 1500 Da in size (approximately 15 amino acids) and to crosslink IgE molecules and to induce an immune response, they must be greater than about 3000 Da in size (approximately 30 amino acids) (Nutten (2018) EMJ Allergy Immunol 3(1): 50-59).

Suitably, therefore, at least about 95%, at least about 98%, at least about 99% or about 100% of the peptides by weight in the eHF have a molecular mass of less than about 3000 Da. There may, for example, be no detectable peptides about 3000 Da or greater in size in the eHF.

Suitably, therefore, at least about 95%, at least about 98%, at least about 99% or about 100% of the peptides by weight in the eHF have a molecular mass of less than about 1500 Da. Preferably, at least 99% of the peptides by weight have a molecular mass of less than about 1500 Da. There may, for example, be no detectable peptides about 1500 Da or greater in size in the eHF.

Preferably, at least about 85%, at least about 90%, at least about 95%, at least about 98% or at least about 99% of the peptides by weight in the eHF have a molecular mass of less than about 1200 Da. More preferably, at least 95% or 98% of the peptides by weight in the eHF have a molecular mass of less than about 1200 Da.

Suitably, at least about 80%, at least about 85%, at least about 90%, or at least about 95% of the peptides by weight in the eHF have a molecular mass of less than about 1000 Da. Preferably, at least about 95% of the peptides by weight in the eHF have a molecular mass of less than about 1000 Da.

Preferably, the eHF has no detectable peptides about 3000 Da or greater in size; and at least about 95% of the peptides by weight have a molecular mass of less than about 1200 Da.

Having a high proportion of di- and tri-peptides may improve nitrogen (protein) absorption, even in patients with gut impairment. PEPT1 is a dedicated facilitator transport route for small peptide absorption (e.g. di- and tri-peptides). In the first weeks of life, intestinal PEPT1 is important for nutritional intake, and later for diet transition following weaning.

Thus, at least about 30%, at least about 40%, or at least about 50% of the peptides by weight in the eHF may, for example, be di- and tri-peptides. Preferably, at least about 45%, at least about 50%, 45-55%, or 50-54% of the peptides by weight in the eHF are di- and tri-peptides. More preferably, about 51-53%, or most preferably, about 52% of the peptides by weight in the eHF are di- and tri-peptides.

Suitably, at least about 30%, at least about 40%, or at least about 50% of the peptides by weight in the eHF have a molecular mass of between 240 and 600 Da. Preferably, at least about 45%, at least about 50%, 45-55%, or 50-54% of the peptides by weight in the eHF have a molecular mass of between 240 and 600 Da. More preferably, about 51-53%, or most preferably, about 52% of the peptides by weight in the eHF have a molecular mass of between 240 and 600 Da.

The peptides in the eHF may, for example, have a median molecular weight of 300 Da to 370 Da, preferably 320 Da to 360 Da.

The principal recognised cow's milk allergens are alpha-lactalbumin (aLA), beta-lactoglobulin (bLG) and bovine serum albumin (BSA).

Suitably, therefore, the eHF may have non-detectable aLA content, for example about 0.010 mg/kg aLA or less; the eHF may have non-detectable bLG content, for example about 0.010 mg/kg bLG or less; and/or the eHF may have non-detectable BSA content, for example about 0.010 mg/kg BSA or less. Preferably, the eHF comprises no detectable amounts of aLA, bLG and BSA. The content of aLA, bLG and BSA may be determined by any method known to those of skill in the art, for example ELISA.

Method of Hydrolysis

Proteins for use in the nutritional composition, preferably the infant formula of the invention, may be hydrolysed by any suitable method known in the art. For example, proteins may be enzymatically hydrolysed, for example using a protease. For example, protein may be hydrolysed using alcalase (e.g. at an enzyme:substrate ratio of about 1-15% by weight and for a duration of about 1-10 hours). The temperature may range from about 40° C. to 60° C., for example about 55° C. The reaction time may be, for example, from 1 to 10 hours and pH values before starting hydrolysis may, for example, fall within the range 6 to 9, preferably 6.5 to 8.5, more preferably 7.0 to 8.0.

Porcine enzymes, in particular porcine pancreatic enzymes may be used in the hydrolysis process. For example, WO1993004593A1 discloses a hydrolysis process using trypsin and chymotrypsin, which includes a two-step hydrolysis reaction with a heat denaturation step in between to ensure that the final hydrolysate is substantially free of intact allergenic proteins. The trypsin and chymotrypsin used in these methods are preparations produced by extraction of porcine pancreas.

WO2016156077A1 discloses a process for preparing a milk protein hydrolysate comprising hydrolysing a milk-based proteinaceous material with a microbial alkaline serine protease in combination with bromelain, a protease from *Aspergillus* and a protease from *Bacillus*.

Free Amino Acids

The nutritional composition of the invention may comprise free amino acids.

The levels of free amino acids may be chosen to provide an amino acid profile that is sufficient for infant nutrition, in particular an amino acid profile that satisfies nutritional regulations (e.g. European Commission Directive 2006/141/EC).

Free amino acids may, for example, be incorporated in the eHF of the invention to supplement the amino acids comprised in the peptides.

Example free amino acids for use in the nutritional composition of the invention include histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof.

Free amino acids provide a protein equivalent source (i.e. contribute to the nitrogen content). As described above, having a high proportion of di- and tri-peptides may improve nitrogen (protein) absorption, even in patients with gut impairment. Accordingly, having a low proportion of free amino acids may also improve nitrogen (protein) absorption, even in patients with gut impairment.

Suitably, therefore, the free amino acids in the eHF may be present in a concentration of 50% or less, 40% or less, 30% or less, or 25% or less by weight based on the total weight of amino acids. Preferably, the eHF comprises 25% or less by weight of free amino acids based on the total weight of amino acids. More preferably, the free amino acids in the eHF are present in a concentration of 20-25%, 21-23%, or about 22% by weight based on the total weight of amino acids.

The free amino acids content may be determined by any method known of skill in the art. Suitably, the free amino acids content may be obtained by separation of the free amino acids present in an aqueous sample extract by ion exchange chromatography and photometric detection after post-column derivatisation with ninhydrin reagent. Total amino acids content may be obtained by hydrolysis of the test portion in 6 mol/L HCl under nitrogen and separation of individual amino acids by ion-exchange chromatography, as described above.

Carbohydrate

The carbohydrate may be any carbohydrate which is suitable for use in a nutritional composition.

The carbohydrate content of the nutritional composition of the invention, particularly the infant formula of the invention, is preferably in the range 9-14 g carbohydrate per 100 kcal.

Example carbohydrates for use in the nutritional composition include lactose, saccharose, maltodextrin and starch. Mixtures of carbohydrates may be used.

In some embodiments, the carbohydrate content comprises maltodextrin. In some embodiments, at least about 20%, at least about 25%, at least about 30%, at least about 35%, at least about 40%, at least about 50%, at least about 60% or at least about 70% by weight of the total carbohydrate content is maltodextrin.

In some embodiments, the carbohydrate content comprises lactose. In some embodiments, at least about 20%, at least about 25%, at least about 30%, at least about 35%, at least about 40%, at least about 50%, at least about 60% or at least about 70% by weight of the total carbohydrate content is lactose.

In some embodiments, the carbohydrate comprises lactose and maltodextrin.

Fat

The fat content of the nutritional composition of the invention, particularly the infant formula of the invention, is preferably in the range 4.0-6.0 g fat per 100 kcal.

Example fats for use in the nutritional composition of the invention include sunflower oil, low erucic acid rapeseed oil, safflower oil, canola oil, olive oil, coconut oil, palm kernel oil, soybean oil, fish oil, palm oleic, high oleic sunflower oil and high oleic safflower oil, and microbial fermentation oil containing long chain, polyunsaturated fatty acids.

The fat may also be in the form of fractions derived from these oils, such as palm olein, medium chain triglycerides (MCT) and esters of fatty acids such as arachidonic acid, linoleic acid, palmitic acid, stearic acid, docosahexaeonic acid, linolenic acid, oleic acid, lauric acid, capric acid, caprylic acid, caproic acid, and the like.

Further example fats include structured lipids (i.e. lipids that are modified chemically or enzymatically in order to change their structure). Preferably, the structured lipids are sn2 structured lipids, for example comprising triglycerides having an elevated level of palmitic acid at the sn2 position of the triglyceride. Structured lipids may be added or may be omitted.

Oils containing high quantities of preformed arachidonic acid (ARA) and/or docosahexaenoic acid (DHA), such as fish oils or microbial oils, may be added.

Long chain polyunsaturated fatty acids, such as dihomo-γ-linolenic acid, arachidonic acid (ARA), eicosapentaenoic acid and docosahexaenoic acid (DHA), may also be added.

Medium Chain Triglycerides (MCTs)

A high concentration of MCT may impair early weight gain. MCT is not stored and does not support fat storage. For instance, Borschel et al. have reported that infants fed formula without MCT gained significantly more weight between 1-56 days than infants fed formulas containing 50% of the fat from MCT (Borschel, M. et al. (2018) Nutrients 10(3): 289).

Thus, about 30% or less by weight of the fat may, for example, be medium chain triglycerides (MCTs) in the nutritional composition of the present invention.

In some embodiments, about 25% or less by weight, 20% or less by weight, 15% or less by weight, 10% or less by weight, 5% or less by weight, 4% or less by weight, 3% or less by weight, 2% or less by weight, 1% or less by weight, 0.5% or less by weight, or 0.1% or less by weight of the fat is medium chain triglycerides (MCTs).

In some embodiments, 0-30% by weight, 0-25% by weight, 0-20% by weight, 0-15% by weight, 0-10% by weight, 0-5% by weight, 0-4% by weight, 0-3% by weight, 0-2% by weight, 0-1% by weight, 0-0.5% by weight, or 0-0.1% by weight of the fat is medium chain triglycerides (MCTs).

In some embodiments, the nutritional composition comprises no added MCTs. Suitably, about 0% by weight of the fat is MCTs and/or the composition comprises no detectable MCTs.

Suitably, the nutritional composition comprises no MCTs.

Further Ingredients

The nutritional composition, particularly an infant formula or young-child formula of the invention, may also contain all vitamins and minerals understood to be essential in the daily diet in nutritionally significant amounts. Minimum requirements have been established for certain vitamins and minerals.

Example vitamins, minerals and other nutrients for use in the nutritional composition of the invention, particularly the infant formula of the invention, include vitamin A, vitamin 1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine and L-carnitine. Minerals are usually added in their salt form.

The nutritional composition may comprise one or more carotenoids.

The nutritional composition may also comprise at least one probiotic. The term "probiotic" refers to microbial cell preparations or components of microbial cells with beneficial effects on the health or well-being of the host. In particular, probiotics may improve gut barrier function.

Examples of probiotic micro-organisms for use in the nutritional composition of the invention include yeasts, such as *Saccharomyces, Debaromyces, Candida, Pichia* and *Torulopsis*; and bacteria, such as the genera *Bifidobacterium, Bacteroides, Clostridium, Fusobacterium, Melissococcus, Propionibacterium, Streptococcus* Preferred probiotics are those which as a whole are safe, are L(+) lactic acid producing cultures and have acceptable shelf-life for products that are required to remain stable and effective for up to 24 months, *Enterococcus, Lactococcus, Staphylococcus, Peptostrepococcus, Bacillus, Pediococcus, Micrococcus, Leuconostoc, Weissella, Aerococcus*, Oenococcus and *Lactobacillus.*

Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei* Shirota, *Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus rhamnosus* (*Lactobacillus* GG), *Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus* and *Staphylococcus xylosus, Lacticaseibacillus rhamnosus, Lacticaseibacillus paracasei, Limosilactobacillia, Akkermemsia, Clostridales, Prevotella* The nutritional composition of the invention may also contain other substances which may have a beneficial effect such as prebiotics, lactoferrin, fibres, nucleotides, nucleosides and the like.

IL-10 and Allergic Sensitisation

The present inventors have surprisingly found that specific combinations of HMOs are most efficacious in inducing Interleukin-10 (IL-10) and thereby have utility in reducing the allergic sensitisation to allergens and inducing tolerance to allergens.

IL-10 is a pleiotropic, immunoregulatory cytokine that is important in protecting the host from allergy, infection-associated immunopathology and autoimmunity.

IL-10 was initially characterized as a T helper (TH) 2 specific; however, further investigations revealed that IL-10 production was also associated with T regulatory (Treg) cell responses.

IL-10-deficient mice exhibit prolonged and exaggerated immune responses toward antigen, in many cases accompanied by excessive inflammation and tissue damage, and they often develop chronic enterocolitis (Kühn et al., 1993, Cell 75, 263-274; Leon et al., 1998, Ann. N.Y. Acad. Sci. 856, 69-75.). Single-nucleotide polymorphisms (SNPs) associated with lower IL-10 mRNA expression are also overrepresented in patients with RA (Hajeer et al., 1998, Scand. J. Rheumatol. 27, 142-145), severe asthma (Lim et al., 1998, Lancet 352, 113,), and SLE (Gibson et al., 2001, J. Immunol. 166, 3915-3922). Thymically and Peripherally Generated FoxP3+ Regulatory T Cells Secrete IL-10 (Sky Ng et al., Front. Immunol., 31 May 2013).

The cytokines IL-4, IL-5, and IL-13, secreted by TH2 cells, provide protective immunity in the context of parasite infection, but also initiate, amplify, and prolong allergic responses by enhancing production of IgE and are responsible for recruitment, expansion, and differentiation of eosinophils and mast cells (Robinson et al., 1992, N. Engl. J. Med. 326, 298-304; Romagnani, 1994, Annu. Rev. Immunol. 12, 227-257; Northrop et al., 2006, J. Immunol. 177, 1062-1069). Early studies of experimental TH2-inducing parasitic infections, including *Trichuris muris* and *T. cruzii* demonstrated a key role for IL-10 in preventing a lethal T cell response (Schopf et al., 2002, J. Immunol. 168, 2383-2392).

TH2-derived IL-10 is associated with downregulation of IL-4 and IL-13 during allergic responses (Grünig et al., 1997, J. Exp. Med. 185, 1089-1100; Jutel et al., 2003, Eur. J. Immunol. 33, 1205-1214; Akdis et al., 2004, J. Exp. Med. 199, 1567-1575). In a mouse model of allergic airway inflammation, IL-10 is crucial in restraining TH2 responses (Grünig et al., 1997). After repeated inhalation of *Aspergillus fumigatus* allergens, lung cells and broncho-alveolar lavage (BAL) fluid from IL-10-knockout mice produced higher levels of IL-4, IL-5, and IFN-γ, leading to exaggerated airway inflammation (Grünig et al., 1997). In addition, alveolar macrophages isolated from asthmatic patients secrete lower levels of IL-10 compared to those from non-asthmatics (Borish, 1998; John et al., 1998, Am. J. Respir. Crit. Care Med. 157, 256-262).

IL-10 plays an important role in mediating successful antigen-specific therapeutic tolerance. For example, intranasal administration of peptide derived from OVA can reduce symptoms of TH2-driven OVA/alum-induced airway hypersensitivity (AHR) (Akbari et al., 2001). Protection from AHR is associated with induction of IL-10-secreting pulmonary DCs with capacity to induce IL-4 and IL-10-secreting OVA-specific CD4+ T cells in vitro (Akbari et al., 2001). Neutralization of IL-10 during tolerance induction results in elevated OVA-specific IgE production and negates the protective effect of OVA administration (Vissers et al., 2004, J. Allergy Clin. Immunol. 113, 1204-1210). Successful allergen-specific immunotherapy (SIT) in man, for example in the treatment of grass pollen or house dust mite allergies, correlates with generation of IL-10-secreting CD4+ T cells (Jutel et al., 2003, Eur. J. Immunol. 33, 1205-1214). IL-10 limits TH2 responses by downregulation of IL-4, inhibition of antigen presentation by MHC class II on DCs, and suppression of co-stimulatory molecule expression including CD28, ICOS, and CD2 (Taylor et al., 2007, J. Allergy Clin. Immunol. 120, 76-83). This is mediated via src homology phosphatase (SHP)-1 in naïve CD4+ T cells, suggesting that IL-10 can regulate effector responses and also prevent the differentiation of TH2 cells from naïve CD4+ T cells (Taylor et al., 2007).

The nutritional composition of the invention may be used to treat, prevent or reduce the risk of an interleukin IL-10 mediated disease. The critical role of IL-10 in immunoregulation goes beyond the prevention of allergic disease and extends to other diseases including inflammatory bowel disease and autoimmune disease. In the context of IBD it has been showed that mice deficient in IL-10 develop spontaneous colitis (Kuhn et al; 1993, Cell. 75, 263-274). This process can be prevented by IL-10 administration or IL-10 overexpression (Steidler et al; 2000, Science. 289, 1352-1355 and Hagenbaugh et al; 1997, J Exp Med. 185, 2101-2110). Similarly, IBD predisposition in humans is strongly associated with defect IL-10 responses (Glocker et al; 2009, N Engl J Med. 361, 2033-2045). The importance of IL-10 in immunoregulation has further been demonstrated in a range of autoimmune pathologies as lack of IL-10 worsened the development of rheumatoid arthritis (Hata et al; 2004, J Clin Invest. 114, 582-588), lupus (Ishida et al; 1994, J Exp Med. 179, 305-310) and encephalomyelitis (Betteli et al; 1998, J Immunol. 161, 3299-3306) in preclinical models.

The nutritional composition of the invention may be used to treat or prevent allergic sensitization to an allergen.

The nutritional composition of the invention may be used to induce tolerance to an allergen.

Examples of allergens include milk protein, egg protein, wheat protein, soya protein, peanut protein, tree nut protein, fish protein, crustacean protein, shellfish protein, and sesame protein. A particularly preferred allergen is cow's milk protein.

The nutritional composition of the invention may be used to speed up outgrowth of an allergy, preferably cow's milk allergy.

The term "allergy" refers to a hypersensitivity of the immune system to a substance which is normally tolerated (an allergen). The allergy may be an allergy detected by a medical doctor. Examples of allergies include food allergy, atopic dermatitis, eczema, asthma and rhinitis. The present invention provides a nutritional composition as described herein for use in reducing such allergies in infants and children, particularly allergies to milk protein, egg protein, wheat protein, soya protein, peanut protein, tree nut protein, fish protein, crustacean protein, shellfish protein, and sesame protein. A particular preferred allergy referred to herein is cow's milk allergy.

The term "allergic sensitisation" refers to sensitisation of the immune system to agents that are normally tolerated and which would typically be harmless in the absence of an allergic response (known as allergens, for example substances in food or pollen). Thus, allergic sensitisation may refer to a priming of the immune system to recognise allergens. Individuals who are sensitised in this way may then develop an allergic reaction on re-exposure to the allergen.

The nutritional composition of the invention may be used to reduce the occurrence of allergic sensitisation in a subject and/or prevent allergic sensitisation in subject. Preferably, the subject is an infant or child.

As used herein, "reduce the occurrence" of allergic sensitisation means that the nutritional composition reduces the likelihood of allergic sensitisation.

As used herein, "prevent" allergic sensitisation means that the subject, e.g. infant, has not yet been sensitised, and the nutritional composition prevents allergic sensitisation.

In some embodiments, the subject, particularly an infant, is at risk of developing one or more allergies. For example, the infant may belong to a family with a history of one or more allergies. Preferably, the nutritional composition of the invention is administered to an infant or child. Preferably the child is a young child between 1 to 3 years of age.

Method of Manufacture

The nutritional composition of the invention may be prepared in any suitable manner.

For example, the nutritional composition described herein may be prepared by blending together the protein source, the carbohydrate source and the fat source in appropriate proportions. If used, the further emulsifiers may be included at this point. The vitamins and minerals may be added at this point but vitamins are usually added later to avoid thermal degradation. Any lipophilic vitamins, emulsifiers and the like may be dissolved in the fat source prior to blending. Water, preferably water which has been subjected to reverse osmosis, may then be mixed in to form a liquid mixture. Commercially available liquefiers may be used to form the liquid mixture. The liquid mixture may then be homogenised.

The liquid mixture may then be thermally treated to reduce bacterial loads. This may be carried out, for example, by means of steam injection, or using an autoclave or heat exchanger, for example a plate heat exchanger.

The liquid mixture may then be cooled and/or homogenised. The pH and solid content of the homogenised mixture may be adjusted at this point.

The homogenised mixture may then be transferred to a suitable drying apparatus such as a spray dryer or freeze dryer and converted to powder. If a liquid nutritional composition is preferred, the homogenised mixture may be sterilised, then aseptically filled into a suitable container or may be first filled into a container and then retorted.

The skilled person will understand that they can combine all features of the invention disclosed herein without departing from the scope of the invention as disclosed.

Preferred features and embodiments of the invention will now be described by way of non-limiting examples.

EXAMPLES

Example 1

Peripheral blood mononuclear cells (PBMCs) were isolated and cultured according to previously published study (Holvoet et al 2013—Int Arch Allergy Immunol 2013; 161:142-154). Buffy coat from blood donations of healthy volunteers were collected at the Transfusion Center of Lausanne (Transfusion interegionnale CRS). Human PBMCs were isolated from buffy coat. Cells were resuspended with equivolume of PBS. The PBMCs were isolated by density gradient centrifugation on Histopaque (Sigma). The cells at the interphase were collected and washed two times with PBS+2% FCS. The PBMCs were re-suspended in complete RPMI 1640 Medium, GlutaMAX™ Supplement (Thermofisher scientific) containing 10% fetal bovine serum (FBS; Thermofisher scientific), 1% penicillin/streptomycin (Sigma). The cells were cultured in 48-well plates (Milian, Meyrin, Switzerland) at $1.5\times10^6$ cells/ml in the presence of 50 ng/ml of IL-4 (Bioconcept) and 1 µg/ml of anti-CD40 antibody (R&D Systems, Abingdon, UK) in cIMDM to induce a Th2 cytokine phenotype. LPS was used at 100 µg/ml. After 3 days of culture, individual and mix of HMOs were added at 100 µg/ml final. After adding ingredients, PBMC culture was continued for an additional 48 h resulting in total culture duration of 5 days.

Il-10 Expression levels are shown in FIG. 1. The combinations of 2FL, 3FL, 3SL and LNnT; and 2FL, 3FL, 3SL, LNnT, 6SL and LNT gave the highest level of IL-10 expression.

Example 2

Dendritic cells (DCs) are critical in mounting adaptive immune responses. In combination with their antigen presentation capabilities, together with providing the correct levels of co-stimulatory molecules, they can direct the fate of T cell responses. Tolerogenic DCs express elevated levels of immunoregulatory cytokines including IL-10, TGF-β and IL-27 and importantly drive the differentiation of Tregs. These tolerogenic DCs can be identified by their reduced levels of co-stimulatory molecules such as CD80, 86 and CD40 as well as increased expression of inhibitory marker PD-L1 (Takenaka et al; 2017, Semi Immunopathol. 39, 113-120).

Figure 2:
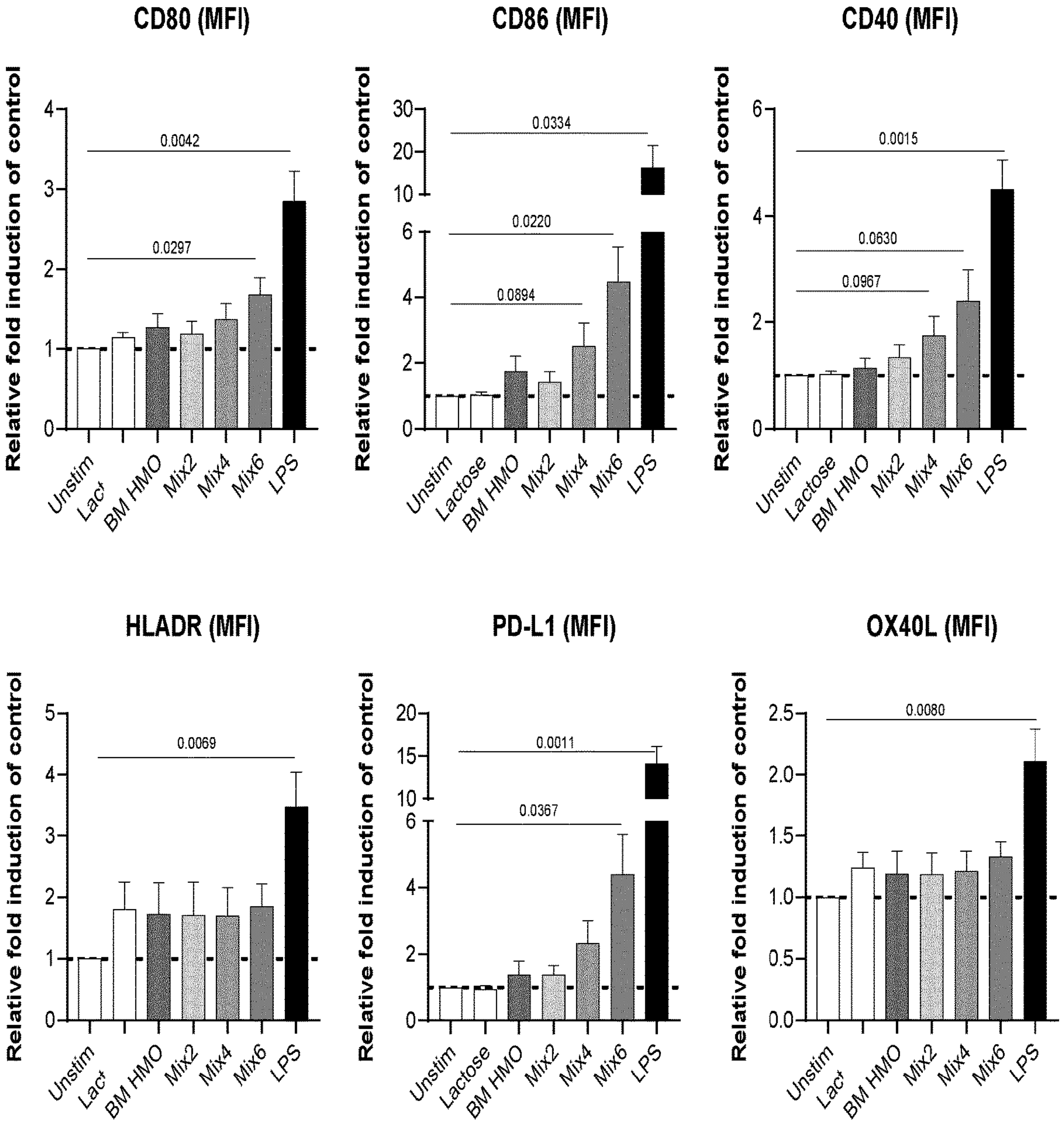
FIG. 2—Induction of tolerogenic markers by mixtures of HMOs according to the invention. Monocytes were isolated from fresh PBMCs and differentiated into DCs in the presence of HMO mixes 2, 4, 6 as well as lactose and HMO derived from breast milk (BM). LPS was used as positive control for the expression of DC markers (CD80, CD86, CD40, HLADR, PD-L1, OX40L). Intermediate expressions relative to LPS are considered as marker for tolerogenic DCs.

For the generation of tolerogenic DCs, monocytes were isolated by PBMCs from healthy donors (as described above) by negative selection using EasySep™ human monocyte isolation kit (STEMCELL Technologies). Monocytes were resuspended at $1\times10^6$ monocytes/ml in EasySep media (STEMCELL Technologies) and differentiated to DCs for 6 days in the presence of Immocult™-ACF dendritic cell differentiation supplement (STEMCELLTechnologies) at 1:100 dilution. After 6 days of culture, mixes of HMOs were added at 100 ug/ml to cultured DCs for 24 hours. Expression of different surface markers (CD80, CD86, CD40, HLA-DR, PD-L1 and OX-40L) were measured by flow cytometry to identify tolerogenic DCs. The mix of 2FL, 3FL, 3SL and LNnT and the mix of 2FL, 3FL, 3SL, LNnT, 6SL and LNT induced tolerogenic levels of DC markers such as CD86, PD-L1 and CD40 FIG. 2.

Figure 3:
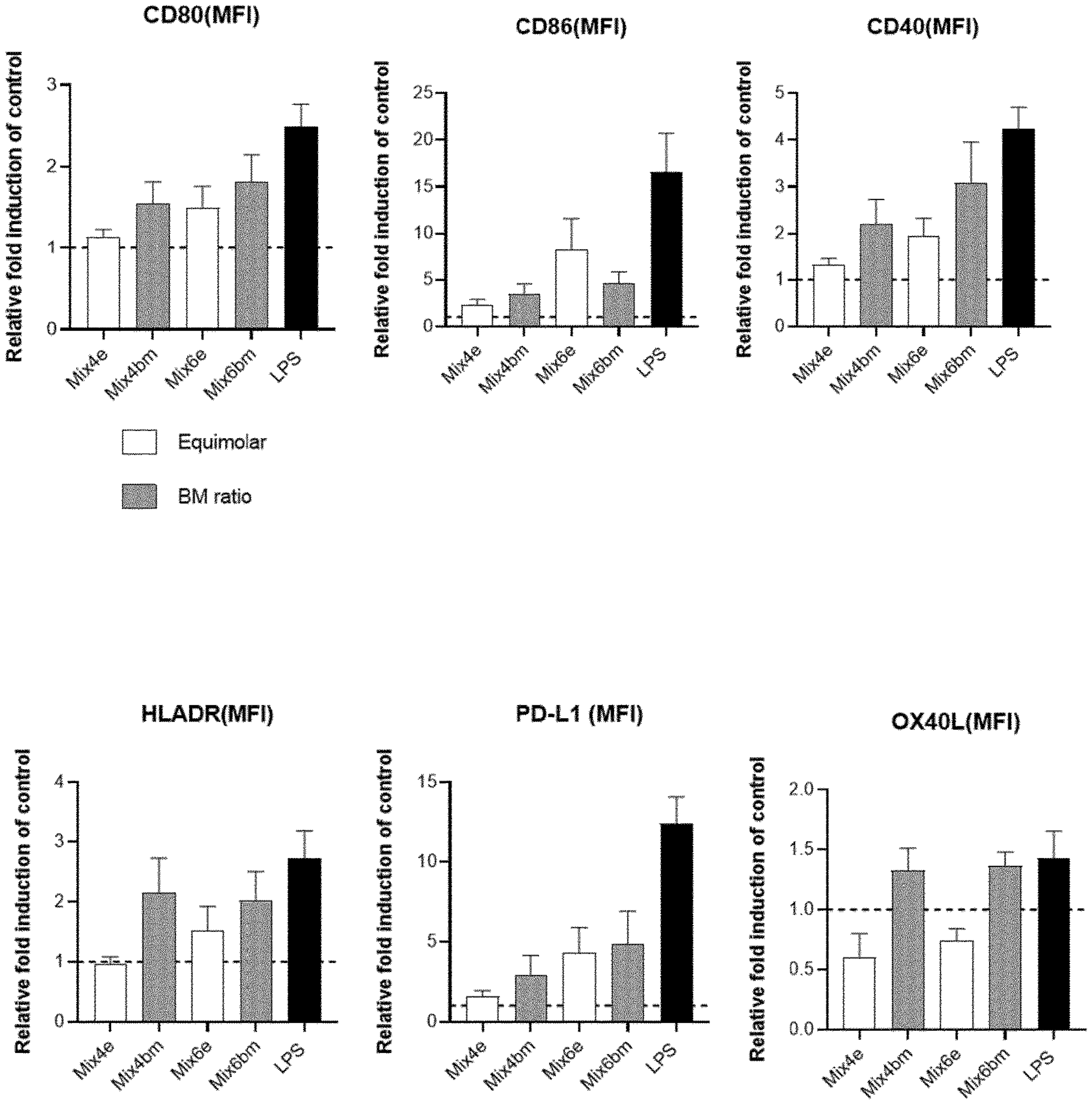
FIG. 3—Induction of tolerogenic markers by mixtures of HMOs according to the invention. Monocytes were isolated from fresh PBMCs and differentiated into DCs in the presence of HMO mixes of 4 and 6 at equimolar ratio or ratio close to breast milk ratio (BM ratio). LPS was used as positive control for the expression of DC markers (CD80, CD86, CD40, HLADR, PD-L1, OX40L) with intermediate expression relative to LPS as a marker for tolerogenic DCs.

Interestingly, the specific ratios 67% 2'FL, 17% 3FL, 8% 3'SL, 7% LNnt for the mix of 4 or 46% 2'FL, 12% 3FL, 6% 3'SL, 12% 6'SL, 5% LNnt, 20% LNT, for the mix of 6, were more efficacious than equimolar ratios of the HMOs in inducing the tolerogenic levels of DC markers such as CD40, HLADR, OX40L and PD-L1, see FIG. 3.

The invention claimed is:

1. A method for inducing tolerance to an allergen, and/or speeding up outgrowth of an allergy, and/or treating or reducing the risk of an interleukin IL-10 mediated disease in an individual in need thereof, the method comprising administering to the individual a nutritional composition comprising human milk oligosaccharides (HMOs), wherein the HMOs comprise 2'-fucosyllactose (2FL), 3'-fucosyllactose (3FL), 3'-sialyllactose (3SL), and lacto-N-neotetraose (LNnT), further wherein the nutritional composition comprises 2FL at about 40 wt % to about 80 wt % 3FL at about 5 wt % to about 30 wt %, 3SL at about 2 wt % to about 15 wt % and the weight ratio of 2FL:LNnT is 1:10 to 12:1, wherein the wt % refers to the total weight of HMOs in the composition.

2. The method according to claim 1, wherein the human milk oligosaccharides (HMOs) in the nutritional composition comprises-consist of 2FL, 3FL, 3SL, and LNnT.

3. The method according to claim 1, wherein the composition comprises 2'-fucosyllactose (2FL), 3'-fucosyllactose (3FL), 3'-sialyllactose (3SL), lacto-N-neotetraose (LNnT), 6'-sialyllactose (6SL) and lacto-N-tetraose (LNT).

4. The method according to claim 3, wherein the HMOs in the nutritional composition consist of 2FL, 3FL, 3SL, LNnT, 6SL and LNT.

5. The method according to claim 1, wherein the HMOs in the nutritional composition comprises:

i. about 40 wt % to about 80 wt % of 2FL;
ii. about 2 wt % to about 15 wt % of LNnT;
iii. about 5 wt % to about 30 wt % 3FL; and
iv. about 2 wt % to about 15 wt % of 3SL.

6. The method according to claim 1, wherein the HMOs in the nutritional composition comprises:

i. about 35 wt % to about 60 wt % of 2FL;
ii. about 1 wt % to about 10 wt % of LNnT;
iii. about 10 wt % to about 30 wt % of LNT;
iv. about 3 wt % to about 20 wt % 3FL;
V. about 1 wt % to about 10 wt % of 3SL; and
vi. about 5 wt % to about 20 wt % of 6SL.

7. The method according to claim 1, wherein the nutritional composition is in a form selected from the group consisting of an infant formula, a starter infant formula, a follow-on or follow-up infant formula, a growing-up milk, a fortifier and a supplement.

8. The method according to claim 1, wherein the total amount of 2FL, 3FL, 3SL, and LNnT present in the nutritional composition is at a concentration of between 10 μg/ml and 10000 μg/ml.

9. The method according to claim 1, wherein the nutritional composition is an extensively hydrolysed formula (eHF) or an amino acid-based formula (AAF).

10. The method according to claim 1, wherein the nutritional composition is an infant or young-child formula and comprises:

(a) 1.6-3.2 g protein per 100 kcal;
(b) 9-14 g carbohydrate per 100 kcal; and
(c) 4.0-6.0 g fat per 100 kcal.

11. The method according to claim 1, wherein the administering of the nutritional composition induces tolerance to an allergen.

12. The method according to claim 1, wherein the administering of the nutritional composition speeds up outgrowth of an allergy.

13. The method according to claim 1, wherein the administering of the nutritional composition treats or reduces the risk of an interleukin IL-10 mediated disease.

14. A synthetic nutritional composition comprising a mixture of human milk oligosaccharides (HMOs), wherein the mixture of HMOs consists essentially of 2'-fucosyllactose (2FL), 3'-fucosyllactose (3FL), 3'-sialyllactose (3SL), and lacto-N-neotetraose (LNnT), wherein the nutritional composition comprises 2FL at about 40 wt % to about 80 wt %, 3FL at about 5 wt % to about 30 wt %, 3SL at about 2 wt % to about 15 wt % and the weight ratio of 2FL:LNnT is 1:10 to 12:1, wherein the wt % refers to the total weight of HMOs in the composition.

15. The nutritional composition according to claim 14, wherein the mixture of HMOs in the nutritional composition consist of:

i. about 40 wt % to about 80 wt % of 2FL;
ii. about 2 wt % to about 15 wt % of LNnT;
iii. about 5 wt % to about 30 wt % 3FL; and
iv. about 2 wt % to about 15 wt % of 3SL.

16. The nutritional composition according to claim 14, wherein the mixture of HMOs in the nutritional composition consist of:

i. about 55 wt % to about 75 wt % of 2FL;
ii. about 4 wt % to about 12 wt % of LNnT;
iii. about 10 wt % to about 25 wt % of 3FL; and
iv. about 4 wt % to about 12 wt % of 3SL.

17. The nutritional composition according to claim 14, wherein the mixture of HMOs in the nutritional composition consist of:

i. about 65 wt % to about 70 wt % of 2FL;
ii. about 6 wt % to about 9 wt % of LNnT;
iii. about 15 wt % to about 20 wt % of 3FL; and
iv. about 7 wt % to about 9 wt % of 3SL.

18. The method according to claim 1, wherein the total amount of 2FL, 3FL, 3SL, and LNnT present in the nutritional composition is at a concentration of between 50 μg/ml and 5000 μg/ml.

19. The method according to claim 1, wherein the allergen is a food allergen.

20. The method according to claim 1, wherein the nutritional composition is capable of being diluted into a liquid composition suitable for feeding an infant or child.

* * * * *